(12) United States Patent
Kaneko (10) Patent No.: US 7,576,774 B2
(45) Date of Patent: Aug. 18, 2009

(54) PHOTOGRAPHY CONTROL APPARATUS AND PROGRAM

(75) Inventor: Takashi Kaneko, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 682 days.

(21) Appl. No.: 11/094,361

(22) Filed: Mar. 31, 2005

(65) Prior Publication Data

US 2005/0219369 A1 Oct. 6, 2005

(30) Foreign Application Priority Data

Mar. 31, 2004 (JP) .............................. 2004-105850

(51) Int. Cl.
H04N 5/225 (2006.01)
H04N 5/222 (2006.01)
H04N 9/47 (2006.01)

(52) U.S. Cl. .............................. 348/207.11; 348/231.3; 348/333.05; 348/92

(58) Field of Classification Search ............ 348/207.11, 348/333.02, 231.3, 211.4, 211.8, 211.99, 348/92, 333.05, 373
See application file for complete search history.

(56) References Cited

U.S. PATENT DOCUMENTS

| | | | |
|---|---|---|---|
| 4,466,721 A | 8/1984 | Detuzzi | |
| 5,485,200 A | 1/1996 | Shimizu | |
| 6,674,485 B2 * | 1/2004 | Akiyama et al. | ............ 348/586 |
| 7,012,636 B2 * | 3/2006 | Hatanaka | ............... 348/211.99 |
| 7,053,936 B2 * | 5/2006 | Imura et al. | ............... 348/231.2 |
| 2001/0052937 A1 * | 12/2001 | Suzuki | ....................... 348/239 |
| 2002/0060295 A1 | 5/2002 | Ikami | |
| 2003/0096322 A1 | 5/2003 | Giuliano et al. | |
| 2003/0214581 A1 | 11/2003 | Ikami | |

FOREIGN PATENT DOCUMENTS

| | | |
|---|---|---|
| DE | 102 02 050 | 7/2003 |
| JP | 11-55563 | 2/1999 |
| JP | 2000-111478 A | 4/2000 |
| JP | 2000111478 | 4/2000 |
| JP | 2000180361 | 6/2000 |
| JP | 2000235003 | 8/2000 |
| JP | 2002-277754 | 9/2002 |
| JP | 2002-310894 | 10/2002 |
| JP | 2003-287497 | 10/2003 |
| JP | 2004233664 | 8/2004 |

OTHER PUBLICATIONS

EP Search Report for EP 05 00 6931 dated Mar. 2, 2006.

* cited by examiner

Primary Examiner—Nhan T Tran
Assistant Examiner—Trung Diep
(74) Attorney, Agent, or Firm—Sughrue Mion, PLLC (57) ABSTRACT

Subjects are repeatedly photographed efficiently and automatically. An input receiving means, for receiving input of photography intervals between completion of a previous photography operation and initiation of a next photography operation; and a photography control means for controlling the photography unit to perform a plurality of photography operations, based on the photography intervals received by the input receiving means; are provided.

22 Claims, 5 Drawing Sheets

Program Exposure Setting (TW)

- Template: program2 (220)
- Sensitivity: Standard
- Exposure Count: 6
- Template Comment: The conditions to apply this program exposure (240)

(210)

| Image 1 | Image 2 | Image 3 | Image 4 |
|---|---|---|---|
| Wait 0 sec (PI) | Wait 0 sec | Wait 0 sec | Wait 0 sec |
| Exposure 1/2sec | Exposure 1sec | Exposure 5 sec | Exposure 10 sec |

| Image 5 | Image 6 | Image 7 | Image 8 |
|---|---|---|---|
| Wait 0 sec | Wait 0 sec | Wait 0 sec | Wait 0 sec |
| Exposure 30 sec | Exposure 1 min | Exposure 1 sec | Exposure 1 sec |

| Image 9 | Image 10 | Image 11 | Image 12 |
|---|---|---|---|
| Wait 0 sec | Wait 0 sec | Wait 0 sec | Wait 0 sec |
| Exposure 1 sec | Exposure 1 sec | Exposure 1 sec | Exposure 1 sec |

| Image 13 | Image 14 | Image 15 | Image 16 |
|---|---|---|---|
| Wait 0 sec | Wait 0 sec | Wait 0 sec | Wait 0 sec |
| Exposure 1 sec | Exposure 1 sec | Exposure 1 sec | Exposure 1 sec |

- File name: experiment1
- File Format: FUJI Img/Inf Format
- Save Folder: C:\LAS3000Image    [Select...]

(230) [Save As Template]  [Reset]  [Close]

FIG.5

Program Exposure Setting — TW

Template: program2 — 220

Sensitivity: Standard

Exposure Count: 7

Template Comment: The conditions to apply this program exposure — 240

Modified — 250

210:

| | | | |
|---|---|---|---|
| Image 1 Wait 0 sec Exposure 1/2sec | Image 2 Wait 0 sec Exposure 1sec | Image 3 Wait 0 sec Exposure 5 sec | Image 4 Wait 0 sec Exposure 10 sec |
| Image 5 Wait 0 sec Exposure 30 sec | Image 6 Wait 0 sec Exposure 1 min | Image 7 Wait 0 sec Exposure 1 sec | Image 8 Wait 0 sec Exposure 1 sec |
| Image 9 Wait 0 sec Exposure 1 sec | Image 10 Wait 0 sec Exposure 1 sec | Image 11 Wait 0 sec Exposure 1 sec | Image 12 Wait 0 sec Exposure 1 sec |
| Image 13 Wait 0 sec Exposure 1 sec | Image 14 Wait 0 sec Exposure 1 sec | Image 15 Wait 0 sec Exposure 1 sec | Image 16 Wait 0 sec Exposure 1 sec |

File name: experiment2 File Format: FUJI Img/Inf Format

Save Folder: C:\LAS3000Image    Select...

230 — Save As Template    Reset    Close

PHOTOGRAPHY CONTROL APPARATUS AND PROGRAM

BACKGROUND OF THE INVENTION

1. Field of the Invention

The present invention relates to a photography system that images a subject, which is provided within a frame.

2. Description of the Related Art

Apparatuses that place subjects within frames, and image the subjects by irradiating the subjects with a light source provided within the frame, are utilized in various fields. For example, a fluorescence detecting system that utilizes fluorescent materials as marker substances is known in the field of biochemistry. The fluorescence detecting system is capable of evaluating gene sequences, levels of gene expression, separation, fixation, molecular weights and characteristics of proteins, and the like, by reading out fluorescence images.

Specifically, fluorescent dyes are added to a solution that includes a plurality of DNA fragments which are to be subjected to electrophoresis. Then, the plurality of DNA fragments are caused to undergo electrophoresis on a gel substrate. Alternatively, a plurality of DNA fragments may be caused to undergo electrophoresis on a gel substrate that contains fluorescent dyes. After the plurality of DNA fragments undergo electrophoresis on the gel substrate, the DNA fragments are marked by soaking the gel substrate in a solution that contains fluorescent dyes or the like. Then, the fluorescent dyes are excited by excitation light, and fluorescence generated by the excitation is detected to form an image. Thereby, the DNA distribution on the gel substrate can be detected.

Alternatively, a plurality of DNA fragments may be caused to undergo electrophoresis on a gel substrate, then denatured. Next, at least a portion of the denatured DNA fragments are transferred onto a transfer substrate such as cellulose nitrate by the Southern Blotting method. A probe, which is prepared by marking a DNA which is complementary to a target DNA with fluorescent dye or by marking RNA with fluorescent dye, is hybridized with the denatured DNA fragments. The DNA fragments, which are complementary to the probe DNA or the probe RNA, are selectively marked. Then, the fluorescent dyes are excited by excitation light, and fluorescence generated by the excitation is detected to form an image. Thereby, the distribution of target DNA on the transfer substrate can be detected.

In recent years, micro array analysis systems are gathering attention as a biochemical analytic system. For example, there are micro array analysis systems that utilize fluorescent materials as marker substances. In these systems, specific bonding materials, which specifically bind with tissue derived substances and of which base sequences and base lengths are known, are spotted on different positions of a carrier such as a glass slide or a membrane filter by a spotter apparatus, thereby forming a plurality of independent spots. The specific bonding materials include: hormones, tumor markers, enzymes, antibodies, antigens, abzymes, other proteins, nucleic acids, cDNA, DNA, and RNA. Next, tissue derived substances, which are collected from tissue by extraction, isolation or the like, or tissue derived substances, which have been chemically processed or chemically modified and marked with a fluorescent marker substance such as fluorescent dyes, are specifically bonded with the specific bonding materials by hybridization or the like. The tissue derived substances include: hormones, tumor markers, enzymes, antibodies, antigens, abzymes, other proteins, nucleic acids, cDNA, DNA, and mRNA. Then, the micro array, on which the specifically bound materials are arranged, is excited by excitation light, and fluorescence generated by the excitation of fluorescent materials and marker substances is photoelectrically detected. Thereby, the tissue derived materials are analyzed.

In addition to the fluorescence methods described above, chemiluminescence methods that utilize chemiluminescence reactions, in which substances emit light during chemical reactions, have also been proposed. The chemiluminescence methods may be employed to inspect and research (genetic analysis, diagnosis, aging) living tissue, or to evaluate deterioration of organic compounds and polymeric compounds. In the chemiluminescence method, for example, tissue derived substances are marked with antigens. Antibodies are marked with marker substances that generate chemical luminescence when they come into contact with chemically luminescent ground substances. The tissue derived substances are brought into contact with the antibodies, then brought into contact with the chemically luminescent ground substances, to generate chemiluminescence.

The fluorescence and the chemiluminescence, which are to be detected in the aforementioned fluorescence methods and the chemiluminescence methods, are extremely faint. Therefore, subjects are hosed within a light shielding frame, and the fluorescence or the chemiluminescence emitted by the subject is detected by a cooled CCD (photography unit), as disclosed in U.S. Patent Application Publication No. 20030214581. Specifically, in the case of the fluorescence method, an excitation light source provided within the frame irradiates excitation light onto the subject. The fluorescence emitted by the subject due to the excitation is focused as a visible image on the cooled CCD via a high sensitivity lens. In the case of the chemiluminescence method, the excitation light source is not activated, and the luminescence emitted by the subject is focused as a visible image on the cooled CCD via the high sensitivity lens.

There are cases in which a single subject is imaged a plurality of times at different photography timings using the above photography apparatus. For these cases, there is a method in which an operator issues photography commands each time that photography is performed, and a method in which photography is automatically repeated at predetermined time intervals. Further, a method has been proposed, in which images are temporarily obtained at predetermined time intervals between initiation and completion of exposure, in Japanese Unexamined Patent Publication No. 2000-111478.

However, in the method in which an operator issues photography commands each time that photography is performed, the burden on the operator is great. In the method in which photography is automatically repeated at predetermined time intervals and in the method disclosed in Japanese Unexamined Patent Publication No. 2000-111478, problems, such as unnecessary image data sets being obtained, and an inability to obtain image data sets at cycles other than the predetermined time intervals, may arise.

SUMMARY OF THE INVENTION

The present invention has been developed in view of the above circumstances. It is an object of the present invention to provide a photography control apparatus and a photography control program, which are capable of efficiently and automatically photographing a subject a plurality of times.

The photography control apparatus of the present invention is an apparatus for controlling a photography apparatus, comprising:

a frame for housing a subject within its interior; and a photography unit for photographing the subject within the frame a plurality of times and for outputting image data sets obtained by each photography operation; the photography control apparatus being characterized by comprising:

input receiving means for receiving input of photography intervals between completion of a previous photography operation and initiation of a next photography operation; and photography control means for controlling the photography unit to perform a plurality of photography operations, based on the photography intervals received by the input receiving means.

The photography control program of the present invention is a program for realizing functions that control a photography apparatus, comprising:

a frame for housing a subject within its interior; and a photography unit for photographing the subject within the frame a plurality of times and for outputting image data sets obtained by each photography operation; the photography control program being characterized by realizing the functions of:

receiving input of photography intervals between completion of a previous photography operation and initiation of a next photography operation; and controlling the photography unit to perform a plurality of photography operations, based on the photography intervals received by the input receiving means.

Here, the input receiving means receives input of photography intervals, that is, the interval between completion of a previous photography operation and initiation of a next photography operation, for the second and later photography operations. The input receiving means may either receive or not receive input of a photography interval for the first photography operation. Here, in the case that a photography interval for the first photography operation is set, a time interval between issuance of a photography command and the initiation of the first photography operation is set.

The "interval between completion of a previous photography operation and initiation of a next photography operation" may be a time interval between a time that the photography unit completes a photography operation and a time that the photography unit initiates a next photography operation. Alternatively, the "interval" may be a time interval between a time that image processes are completed on an image data set obtained by the photography unit and a time that the photography unit initiates a next photography operation.

The photography control apparatus may further comprise storage means for storing a plurality of template data sets, in which photography intervals are set in advance. In this case, the input receiving means reads out one of the template data sets from the storage means and receives input of the photography intervals, which is set in the template data set.

Further, the input receiving means may have a function of correcting the photography intervals, which are set in the template data sets. In this case, the photography control means may control the photography unit to perform the plurality of photography operations, based on the corrected photography intervals which are set in the corrected template data sets. Note that the correction of the photography intervals may be administered on a portion or on all of the photography intervals which are set in the template data sets.

The photography control apparatus may further comprise a display unit and display control means for displaying the photography intervals, which are received by the input receiving means, on the display unit.

Note that the display control means may have a function of displaying that the template data set has been corrected, in the case that the input receiving means corrects the template data set.

Further, the display control means may have a function of displaying the image data sets, which have been obtained by the photography unit. In this case, the display control means may display the image data sets on the display unit, correlated with the photography intervals at which the image data sets were obtained.

The photography control apparatus and the photography control program of the present invention perform the functions of receiving input of photography intervals between completion of a previous photography operation and initiation of a next photography operation; and controlling the photography unit to perform a plurality of photography operations, based on the photography intervals received by the input receiving means. Therefore, users are enabled to set desired photography timings for each photography operation during repeated photography of a subject. Accordingly, problems such as obtainment of unnecessary image data sets and an inability to obtain desired image data sets are prevented, and efficient and automatic photography of a subject a plurality of times becomes possible.

Note that the photography control apparatus may further comprise: storage means for storing a plurality of template data sets, in which photography intervals are set in advance; wherein: the input receiving means reads out one of the template data sets from the storage means and receives input of the photography intervals, which is set in the template data set. In this case, users are not required to set the photography intervals every time that repeated photography is to be performed. Accordingly, the photography intervals are enabled to be set efficiently.

In addition, the input receiving means may have a function of correcting the photography intervals, which are set in the template data sets. In this case, the photography control means may control the photography unit to perform the plurality of photography operations, based on the corrected photography intervals which are set in the corrected template data sets. If this configuration is adopted, setting of the image intervals is facilitated when users desire to correct a portion of the template data sets, because it is not necessary to re-input the photography intervals for each photography operation.

Further, the photography control apparatus may further comprise: a display unit; and display control means for displaying the photography intervals, which are received by the input receiving means, on the display unit. In this case, the display control means may have a function of displaying that the template data set has been corrected, in the case that the input receiving means corrects the template data set. If this configuration is adopted, whether the template data set to be utilized for repeated photography has been corrected can be confirmed easily, without referring to each of the plurality of photography intervals set within the template data set. Therefore, the convenience for users is improved.

Still further, the display control means may have a function of displaying the image data sets, which have been obtained by the photography unit. In this case, the display control means may display the image data sets on the display unit, correlated with the photography intervals at which the image data sets were obtained. If this configuration is adopted, users are enabled to view the image data sets and the photography intervals simultaneously. Therefore, the convenience for users is further improved.

DESCRIPTION OF THE PREFERRED EMBODIMENTS

Figure 1:
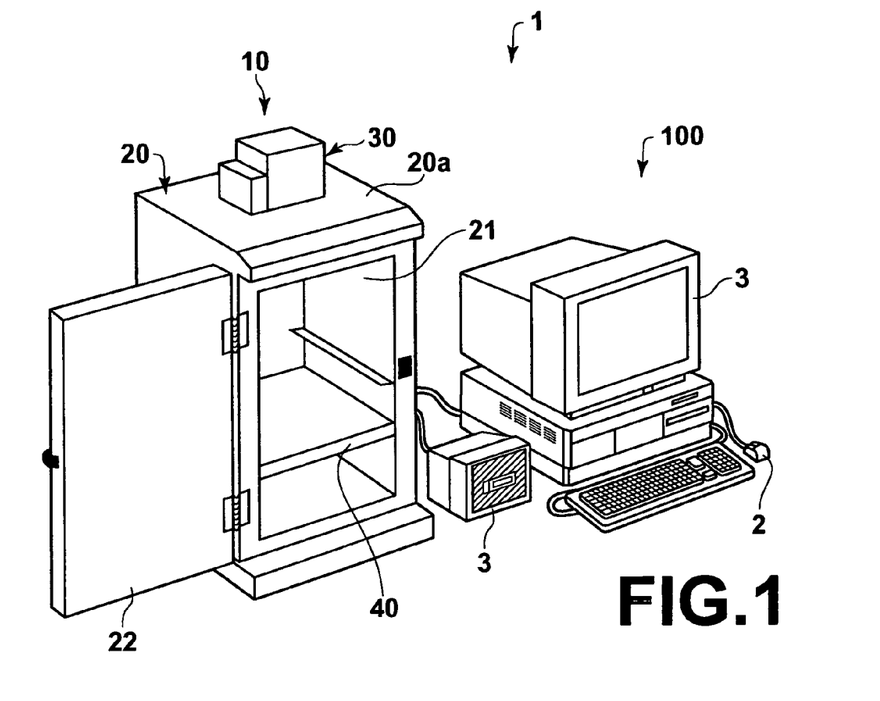
FIG. 1 is a perspective view of a photography system that utilizes the photography control apparatus of the present invention.

Hereinafter, an embodiment of the photography control apparatus of the present invention will be described with reference to the attached drawings. FIG. 1 is a perspective view of a photography system 1 that utilizes the photography control apparatus of the present invention. The photography system 1 is a fluorescence detecting system for displaying fluorescence images by irradiating excitation light onto subjects, which are fluorescent materials. The photography system 1 comprises a photography apparatus 10 and a photography control apparatus 100. The photography apparatus 10 and the photography control apparatus 100 are to be used on a desktop. The photography control apparatus 100 may be a personal computer, for example, which is connected to input means 2, such as a mouse and a keyboard, and a display unit 3, such as a CRT or LCD monitor. The photography apparatus 10 photographs a subject PS and transmits image data sets of the subject PS to the photography control apparatus 100. The photography control apparatus 100 administers image processes on the image data sets, and displays the image data sets on the display unit 3.

Note that the subject may be a test substance that emits luminescence when it comes into contact with a chemically luminescent ground substance (chemiluminescence method). Alternatively, the subject may be test substance which is marked with fluorescent dye that emits fluorescence when irradiated by excitation light (fluorescence method).

Figure 2:
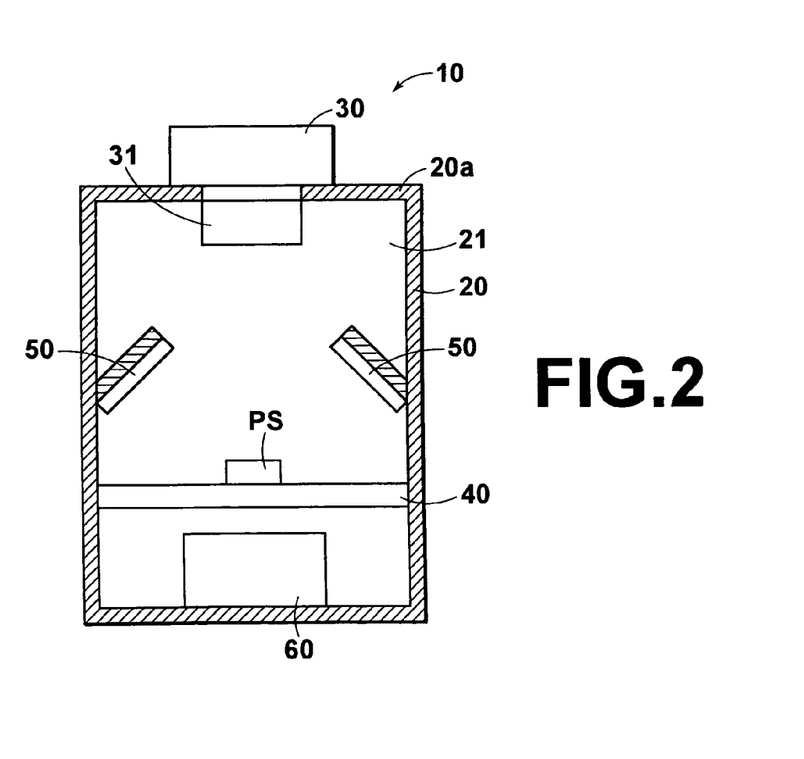
FIG. 2 is a schematic view that illustrates a preferred embodiment of a photography apparatus in the photography system of the present invention.

FIG. 2 is a schematic view that illustrates a preferred embodiment of the photography apparatus 10 in the photography system 1 of the present invention. The photography apparatus 10 illustrated in FIG. 2 comprises: a frame 20; and a photography unit 30. The frame 20 houses subjects therein. The photography unit 30 photographs subjects which are housed within the frame 20, and outputs image data sets.

Here, the frame 20 is formed substantially as a parallelepiped having a hollow portion 21. A subject placement unit 40, on which subjects PS are placed, is provided in the interior of the frame 20. A lid 22 is removably attached to the frame 20, to enable users to open the lid 22 and place subjects inside the frame 20. In this manner, the frame 20 is constituted to be a darkroom, having the hollow portion 21 into which external light does not enter. Therefore, photography is enabled even if the light emitted from the subject is faint.

The photography unit 30 is fixed on the upper surface 20a of the frame 20. The photography unit 30 is configured to photograph the subject PS, which is placed within the frame 20, and to output image data sets. A cooling unit (not shown) is mounted on the photography unit 30. The cooling unit is provided to cool the photography unit 30, to prevent noise components due to dark current from being included in image data sets obtained thereby. A lens unit 31, which is to be focused on the subject PS, is mounted on the photography unit 30. Incident light sources 50 and a bottom light source 60 are provided within the frame 20. The incident light sources 50 irradiate excitation light onto the subject PS, which is a luminescent material, to cause the subject PS to emit light. The incident light sources 50 are provided above the subject placement unit 40. The bottom light source 60 irradiates excitation light onto the subject from below.

Figure 3:
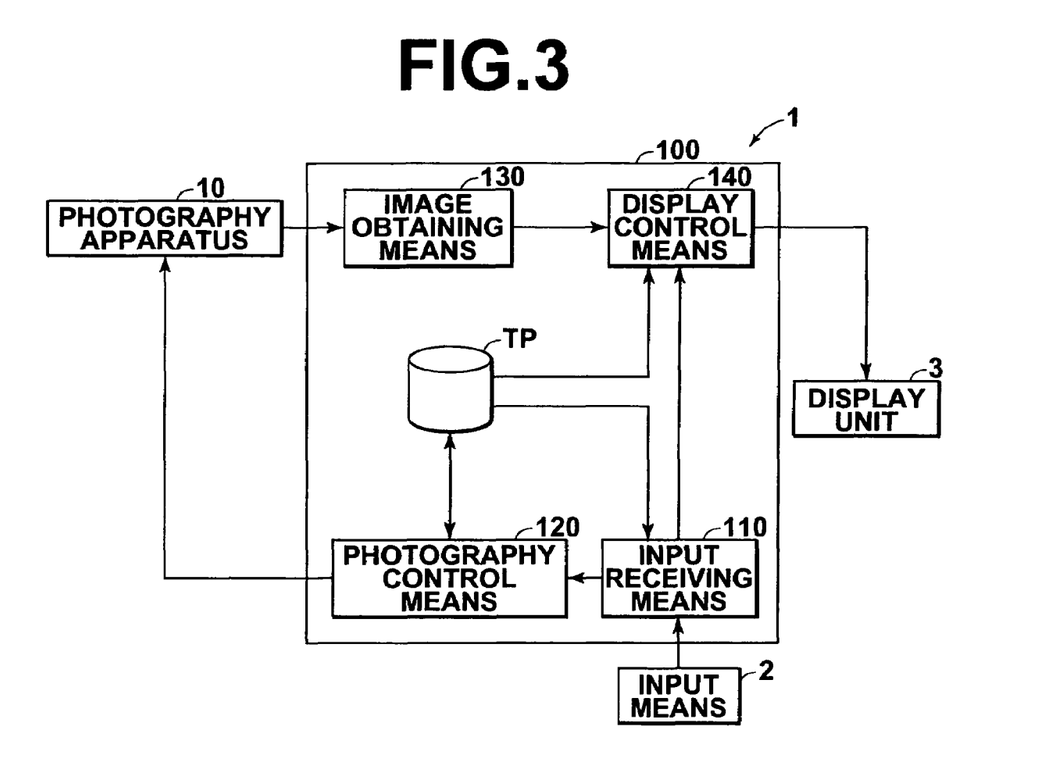
FIG. 3 is a block diagram that illustrates a preferred embodiment of the photography control apparatus according to the present invention.

FIG. 3 is a schematic view that illustrates a preferred embodiment of the photography control apparatus 100 according to the present invention. The photography control apparatus 100 will be described with reference to FIG. 1 and FIG. 3. Note that the structures of the photography control apparatus 100 illustrated in FIG. 3 are realized by executing a photography control program, which is written into an auxiliary memory apparatus, on a computer (for example, a personal computer). Alternatively, the photography control program may be recorded in data recording media such as CD-ROM's and distributed, or distributed via networks such as the Internet, and installed on computers.

The photography control apparatus 100 controls the photography apparatus 10 to perform a plurality of photography operations to image the subject PS. The photography control apparatus 100 comprises: input receiving means 110; photography control means 120, display control means 140; and image obtaining means 130. The input receiving means 110 receives input of photography intervals, that is, time intervals between completion of a previous photography operation and initiation of a next photography operation, for each photography operation. The photography control means 120 controls the photography unit 30 to perform a plurality of photography operations at the photography intervals received by the input receiving means 110. The display control means 140 displays the photography intervals received by the input receiving means 110 on the display unit 3. The image obtaining means 130 obtains image data sets, which have been imaged by the photography apparatus 10.

Figure 4:
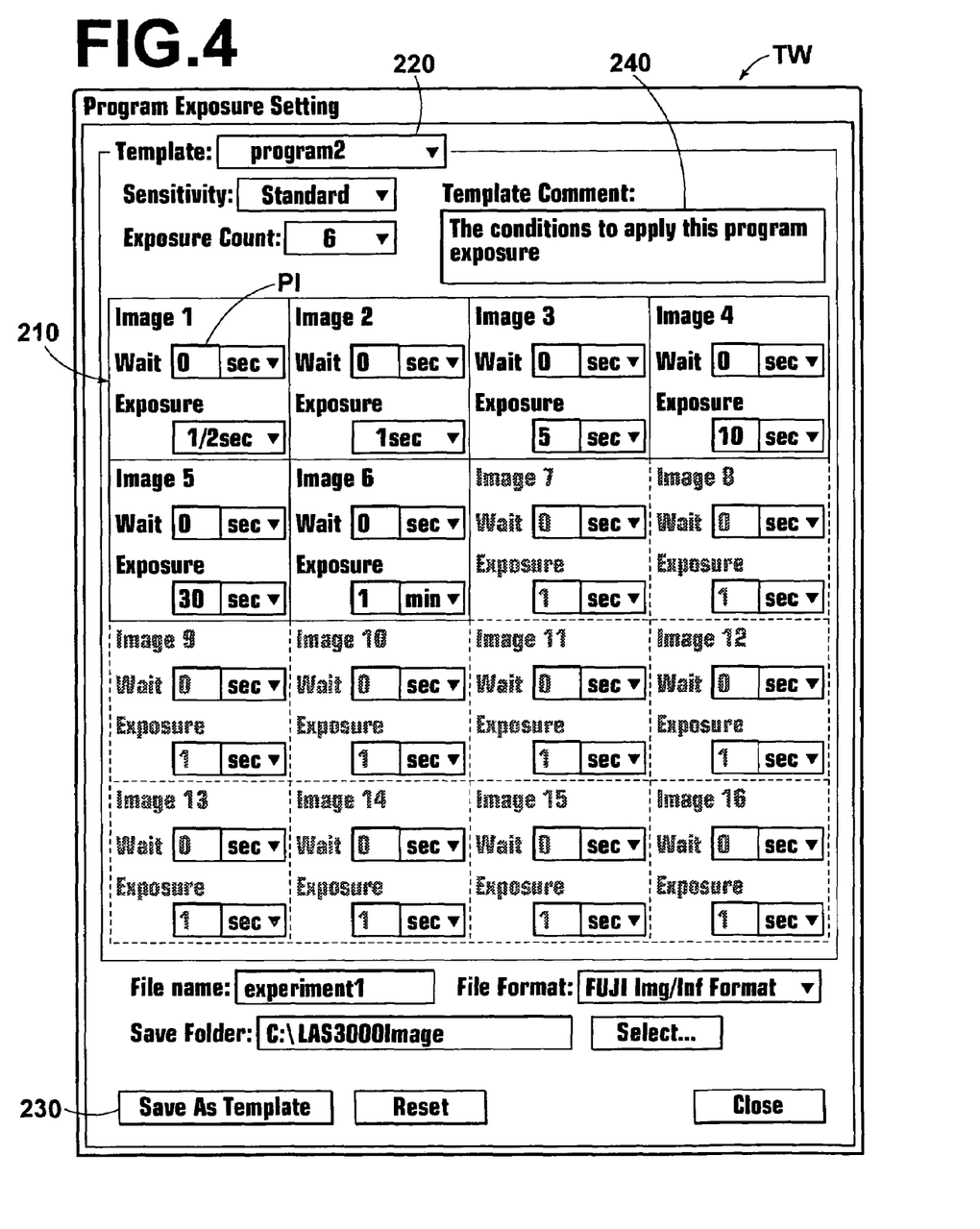
FIG. 4 is a model drawing of an example of a screen which is displayed by a display control means of the photography control apparatus of the present invention.

The display control means 140 is configured to display a photography condition setting window TW, as illustrated in FIG. 4, during reception of the time intervals by the input receiving means 110. Input is received from the input means 2. In FIG. 4, the photography condition setting window TW comprises a plurality of condition setting frames 210. Each of the condition setting frames enables setting of a photography interval PI and an exposure time. When an exposure count (number of times photography is to be performed) is specified, the same number of frames 210 are activated. The input receiving means 110 receives input of the photography intervals PI and the exposure times within the frames 210 from the input means 2.

In this manner, users are enabled to set photography timings for each photography operation as desired, when performing repeated photography. Therefore, problems such as obtainment of unnecessary image data sets and an inability to obtain desired image data sets are prevented, and efficient and automatic photography of a subject a plurality of times becomes possible.

The photography control apparatus 100 illustrated in FIG. 3 further comprises storage means TP, in which a plurality of template data sets are stored. The template data sets have photography intervals for each photography operation set therein in advance. The input receiving means 110 is configured to read out a template data set from within the storage means TP, and to receive input of each of the photography intervals which are set in the template data set.

Specifically, the photography condition setting window TW comprises a template combination box 220, which is used to select a template data set to be utilized. The template combination box 220 is configured to display the names of the plurality of template data sets so that they are selectable. When a user selects a template data set from the template combination box 220 by using the input means 2, the photography sensitivity, the number of photography operations, the photography intervals PI and the exposure times, which are preset in the template data set, are automatically input into the condition setting frames 210. The input receiving means 110 is configured to receive input of the photography intervals PI, which are preset in the template data set. Thereby, the need for users to perform setting of the photography conditions when performing repeated photography is obviated. Accordingly, it is not necessary to input complex photography conditions for each repeated photography operation, and setting of the photography intervals can be performed efficiently. In addition, erroneous input can be eliminated, and experimental protocols can be uniformized, by employing the template data sets.

Note that additional information, such as comments regarding subjects on which a template data set is used, and characteristics of the template data set, are included in the template data sets, along with the photography sensitivity, the number of photography operations, the photography intervals, and exposure times. The additional information is displayed in a template comment box 240.

There are cases in which users set the photography sensitivity, the number of photography operations, the photography intervals PI, and the exposure times, without using the template data sets. In these cases, users may press a "Save As Template" button 230, to save the settings for the photography sensitivity, the number of photography operations, the photography intervals PI and the exposure times, as a template data set.

Further, the input receiving means 110 has a function of receiving corrections to the photography intervals which are set in the template data sets. The photography control means 120 is configured to control the photography unit to photograph the subject PS at the photography intervals which are set in the corrected template data sets. Specifically, when a template data set is selected as described above, the photography sensitivity, the number of photography operations, the photography intervals PI, and the exposure times, which are set in the template data set, are automatically input to the frames 210. At this time, the photography sensitivity, the number of photography operations, and the photography intervals PI and the exposure times within each condition setting frame 210 are correctable. The input receiving means 110 is configured to receive settings of a corrected template data set, if users use the input means 2 to correct a portion or the entirety of the photography sensitivity, the number of photography operations, the photography intervals and the exposure times. Therefore, in cases that a portion of the template data set is desired to be corrected, it is not necessary to re-input values for each photography operation. Accordingly, the setting of photography conditions is facilitated.

Figure 5:
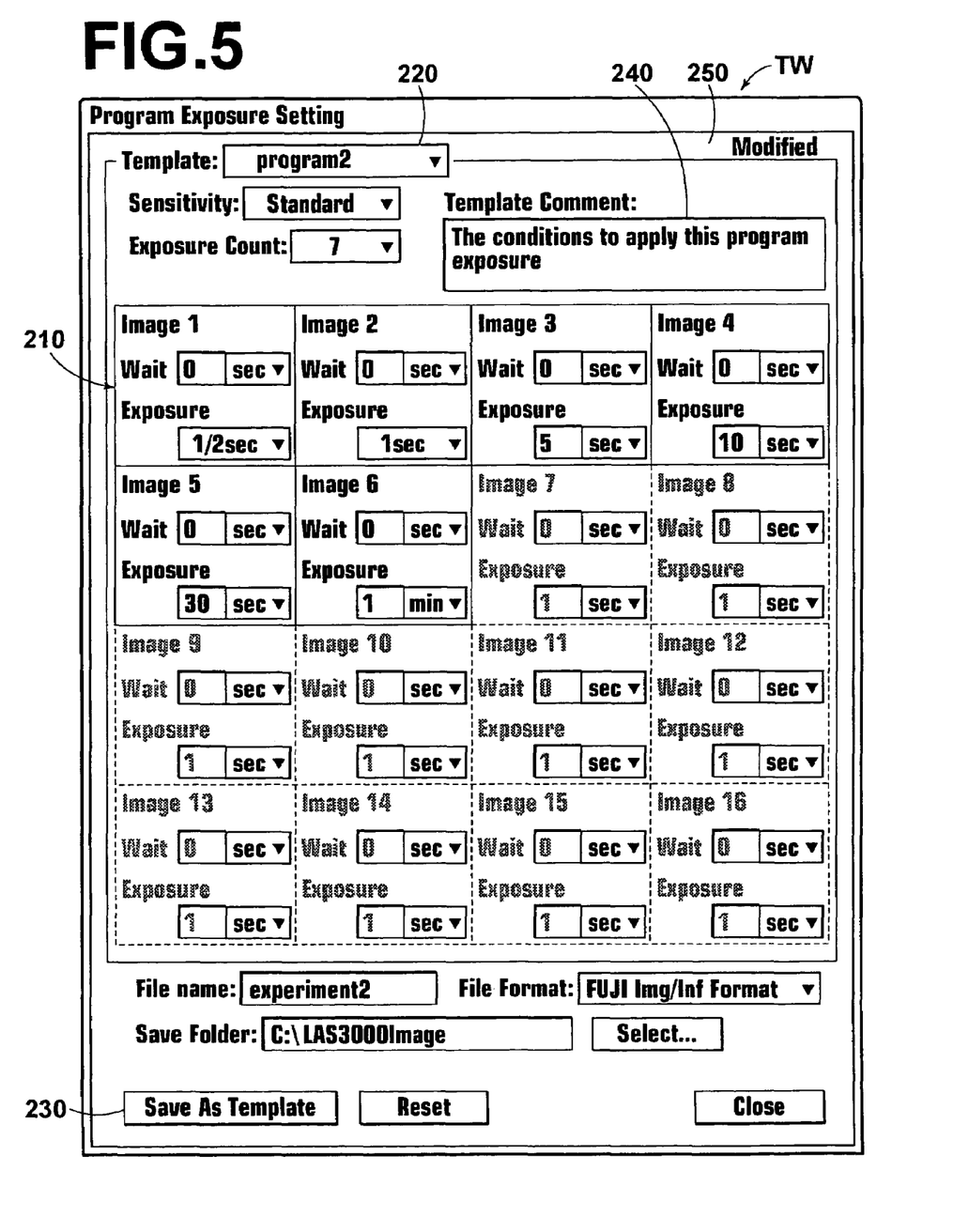
FIG. 5 is a model drawing of another example of a screen which is displayed by a display control means of the photography control apparatus of the present invention.

Further, the display control means 140 has a function of displaying that template data sets have been corrected on the display unit 3, in the case that the input receiving means 110 receives corrections to the template data sets, as illustrated in the upper right corner of FIG. 5, for example. Thereby, whether a template data set to be utilized for repeated photography has been corrected can be confirmed easily, without referring to each of the plurality of photography intervals set within the template data set. Therefore, the convenience for users is improved.

Figure 6:
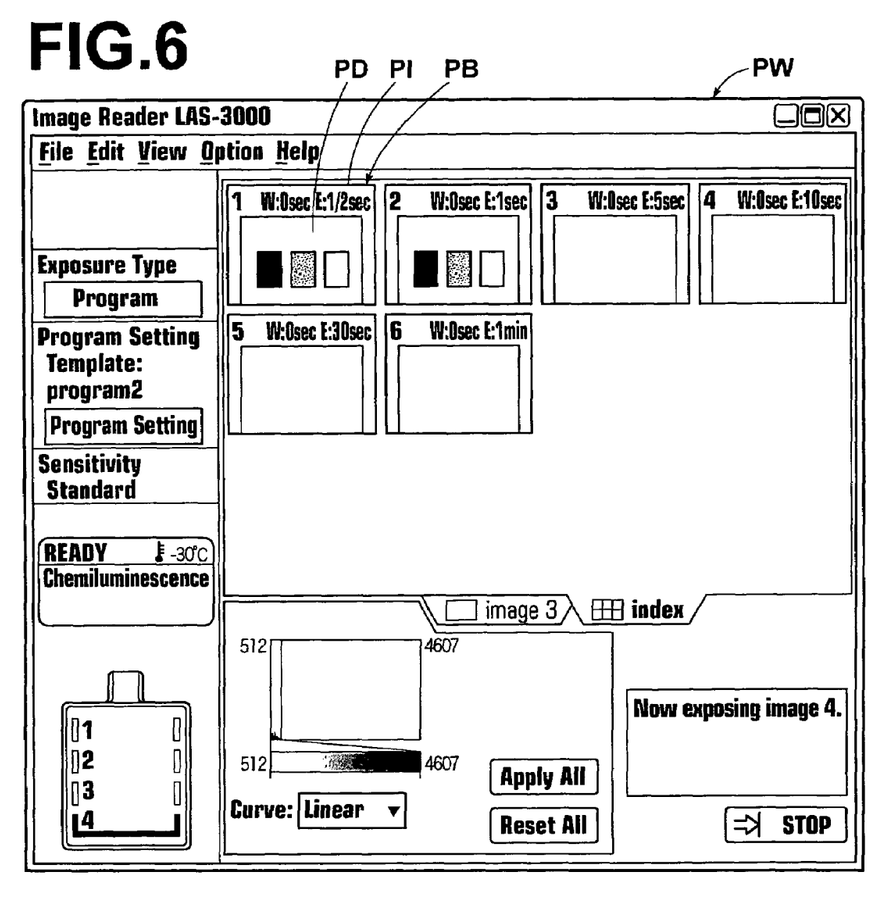
FIG. 6 is a model drawing of still another example of a screen which is displayed by a display control means of the photography control apparatus of the present invention.

The display control means 140 also has a function of displaying image data sets, which have been obtained by the photography unit 30, on the display unit 3. The display control means 140 is configured to display a plurality of image data sets, correlated with the photography intervals and the exposure times during obtainment thereof. Specifically, the display control means 140 has a function of displaying a preview window PW, in which a plurality of image data sets are arranged, on the display unit 3, as illustrated in FIG. 6. The display control means 140 is configured to display an image data set PD within a picture box PB of the preview window PW, every time that the image obtaining means 130 obtains an image data set from the photography apparatus 10. Further, the display control means 140 is configured to display the photography interval PI and the exposure time which were employed during photography of the image data set in the picture box PB. Thereby, users are enabled to confirm both the image data set and the photography interval simultaneously. Accordingly, the convenience for users is improved. Note that if users select a picture box PB within the preview window, the image data set within the picture box PB is enlarged and displayed.

Note that the display control means 140 first displays the same number of picture boxes PB as the number of photography operations, which is set in the condition setting window TW, in the preview window PW. Then, as the image obtaining means 110 obtains image data sets PD, the image data sets PD are displayed within the picture boxes PB. This configuration enables users to recognize how many photography operations remain, during repeated photography.

Figure 7:
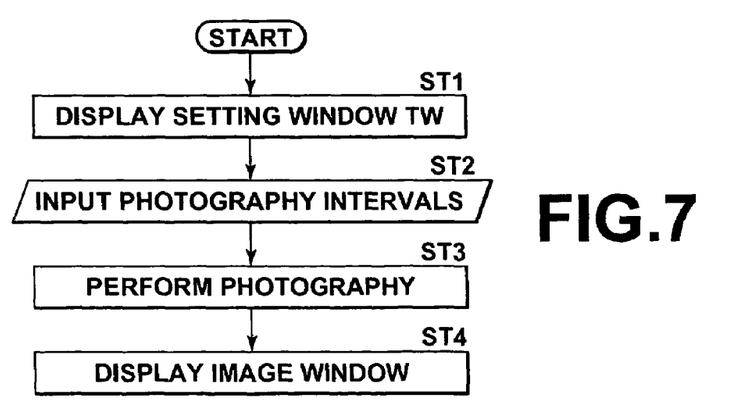
FIG. 7 is a flow chart that illustrates the processes performed by the photography control apparatus of FIG. 3.

FIG. 7 is a flow chart that illustrates an example of the processes performed by the photography control apparatus 100. The processes performed by the photography control apparatus 100 will be described with reference to FIGS. 1 through 7. First, the display control means 140 displays the condition setting window TW on the display unit 3, as illustrated in FIG. 4 (step ST1). A user inputs photography intervals PI and exposure times in each condition setting frame 210, or selects a template data set from the template combination box 220 (step ST2). Then, the input receiving means 110 receives the photography sensitivity, the number of photography operations, the photography intervals PI and the exposure times, and the photography control means 120 causes the photography apparatus 10 to perform photography of the subject PS according to the input settings (step ST3). Specifically, when users issue commands to initiate photography, photography is performed with the exposure time set within the condition setting frame 210 for Image 1, after the photography interval PI for Image 1 has passed, as illustrated in FIG. 4. Thereafter, readout of image data sets from the photography unit 30 and data processes, such as image processes, are performed.

Note that in FIG. 4, the photography intervals PI are time intervals that begin after readout of data from the photography unit 30 and data processes, such as image processes, are completed. Alternatively, the photography intervals PI may be time intervals that begin immediately following completion of photography by the photography unit 30.

Thereafter, the display control means 140 causes image data sets to be displayed within the picture boxes PB of the preview window PW illustrated in FIG. 6, along with the photography intervals PI and the exposure times, every time that the image obtaining means 130 obtains an image data set from the photography apparatus 10.

After the data processes, which are administered on the image data set obtained by the first photography operation, are completed and the photography interval PI set for Image 2 has passed, photography of Image 2 is performed, with the exposure time set therefor (refer to FIG. 4). Photography operations and display of images are repeated for the number of photography operations, which has been set by users (step ST3, step ST4).

The photography control apparatus according to the embodiment described above comprises: the input receiving means 110, for receiving input of photography intervals between completion of a previous photography operation to initiation of a next photography operation; and the photography control means 120, for controlling the photography unit 30 to perform a plurality of photography operations according to the photography intervals which have been received by the input receiving means 110. Therefore, users are enabled to set desired photography timings for each photography operation during repeated photography of a subject. Accordingly, problems such as obtainment of unnecessary image data sets and an inability to obtain desired image data sets are prevented, and efficient and automatic photography of a subject a plurality of times becomes possible.

Note that the photography control apparatus may further comprise: the storage means TP for storing a plurality of template data sets, in which photography intervals are set in advance, as illustrated in FIG. 3. In this case, the input receiving means 110 reads out one of the template data sets from the storage means TP and receives input of the photography intervals, which is set in the template data set. If this configuration is adopted, users are not required to set the photography intervals every time that repeated photography is to be performed. Accordingly, the photography intervals are enabled to be set efficiently.

Further, the input receiving means 110 may have a function of correcting the photography intervals, which are set in the template data sets. In this case, the photography control means 120 may control the photography unit to perform the plurality of photography operations, based on the corrected photography intervals which are set in the corrected template data sets. If this configuration is adopted, setting of the image intervals is facilitated when users desire to correct a portion of the template data sets, because it is not necessary to re-input the photography intervals for each photography operation.

Further, the photography control apparatus may further comprise: the display unit 3; and the display control means 140 for displaying the photography intervals, which are received by the input receiving means 110, on the display unit 3. In this case, the display control means 140 may have a function of displaying that the template data set has been corrected, in the case that the input receiving means corrects the template data set, as illustrated in FIG. 5. If this configuration is adopted, whether the template data set to be utilized for repeated photography has been corrected can be confirmed easily, without referring to each of the plurality of photography intervals set within the template data set. Therefore, the convenience for users is improved.

Still further, the display control means 140 may have a function of displaying the image data sets, which have been obtained by the photography unit. In this case, the display control means may display the image data sets on the display unit, correlated with the photography intervals at which the image data sets were obtained. If this configuration is adopted, users are enabled to view the image data sets and the photography intervals simultaneously. Therefore, the convenience for users is further improved.

Note that the present invention is not limited to the embodiment described above. A warning indicating that settings are not within allowable ranges may be output from the display control means 140 to the display 3, in the case that an exposure time of 50 hours is set, for example.

In addition, the display control means 140 may display the last image data set obtained, from among a plurality of image data sets, with different gradation in the picture box PB illustrated in FIG. 6.

Further, a "Stop" button, for causing photography to be ceased, may be provided in the preview window PW of FIG. 6. If users press the "Stop" button, the photography control means 140 causes the photography unit 30 to cease photography operations.

What is claimed is:

1. A photography control apparatus, for controlling a photography apparatus comprising:
   a frame for housing a subject within an interior of the frame; and
   a photography unit for photographing the subject within the frame a plurality of times and for outputting image data sets obtained by each photography operation; the photography control apparatus comprising:
   input receiving means for receiving input of photography intervals between completion of a previous photography operation and initiation of a next photography operation;
   photography control means for controlling the photography unit to perform a plurality of photography operations, based on the photography intervals received by the input receiving means;
   a display unit;
   display control means for displaying a photography condition setting interface which comprises a plurality of condition setting frames, each of the plurality of condition setting frames corresponding to a single photography operation of the plurality of photography operations, wherein a single image is obtained during the single photography operation; and
   storage means for storing a plurality of template data sets, each of which includes photography intervals for each photography operation set in advance by each template data set; wherein:
   the input receiving means reads out one of the template data sets from the storage means and receives input of the photography intervals, which is set in the template data set.

2. A photography control apparatus as defined in claim 1, further comprising:
   display control means for displaying the photography intervals, which are received by the input receiving means, on the display unit.

3. A photography control apparatus as defined in claim 1, wherein:
   the input receiving means has a function of editing the photography intervals, which are set in the template data sets; and
   the photography control means controls the photography unit to perform the plurality of photography operations, based on the edited photography intervals which are set in the edited template data sets.

4. A photography control apparatus as defined in claim 3, wherein:
the display control means has a function of displaying that the template data set has been edited, in the case that the input receiving means corrects the template data set.

5. A photography control apparatus as defined in claim 4, wherein:
the display control means has a function of displaying the image data sets, which have been obtained by the photography unit.

6. A photography control apparatus as defined in claim 5, wherein:
the display control means displays the image data sets on the display unit, correlated with the photography intervals at which the image data sets were obtained.

7. A photography control apparatus as defined in claim 1, wherein a number of condition setting frames are activated in the photography condition setting interface according to an exposure count which indicates a number of times photography is to be performed and corresponds to a number of photography operations to be performed.

8. A photography control apparatus as defined in claim 7, wherein the photography condition setting interface includes an exposure count input for inputting the exposure count for activating the number of condition setting frames corresponding thereto.

9. A photography control apparatus as defined in claim 7, wherein each condition setting frame includes a photography interval input for inputting the photography interval which corresponds to the photography operation of the condition setting frame.

10. A photography control apparatus as defined in claim 9, wherein each condition setting frame further includes an exposure time input for inputting an exposure time for irradiating excitation light from an excitation light source onto the subject during the corresponding photography operation of the condition setting frame, the exposure time being controlled by the photography control means during photography.

11. A photography control apparatus as defined in claim 1, wherein each condition setting frame includes a photography interval input for inputting the photography interval which corresponds to the photography operation of the condition setting frame.

12. A photography control apparatus as defined in claim 11, wherein the photography interval of each photography operation of the plurality of photography operations is independently input according to each corresponding condition setting frame.

13. A photography control apparatus as defined in claim 11, wherein the photography interval is applied before performing the corresponding photography operation of the condition setting frame.

14. A photography control apparatus as defined in claim 11, wherein the photography interval is applies after performing the corresponding photography operation of the condition setting frame.

15. A photography control apparatus as defined in claim 11, wherein each condition setting frame further includes an exposure time input for inputting an exposure time for irradiating excitation light from an excitation light source onto the subject during the corresponding photography operation of the condition setting frame, the exposure time being controlled by the photography control means during photography.

16. A photography control apparatus as defined in claim 1, wherein each template data set of the plurality of template data sets is stored according to a template title corresponding to a unique subject to be photographed.

17. A photography control apparatus as defined in claim 1, wherein each template data set includes an exposure count, which activates a predetermined number of condition setting frames, and preset photography intervals each setting the photography interval corresponding to each photography operation of the predetermined number of condition setting frames.

18. A photography control apparatus as defined in claim 17, wherein each template data set includes photography intervals and exposure times which are automatically input into the plurality of condition setting frames for each photography operation.

19. A photography control apparatus as defined in claim 18, wherein each template data set further includes a photography sensitivity for photographing by the photography unit.

20. A photography control apparatus as defined in claim 3, wherein the plurality of template data sets each include photography intervals for each photography operation of the plurality of photography operations corresponding to a respective condition setting frame, the photography intervals set in advance by each template data set, and
the editing of the photography intervals set in the template data sets is administered to at least a portion of the photography intervals of the condition setting frames of a selected template data set.

21. A photography control apparatus as defined in claim 20, wherein an edited template data set is stored in the storage means as a new template data set.

22. A photography control apparatus, for controlling a photography apparatus comprising:
a frame for housing a subject within an interior of the frame; and
a photography unit for photographing the subject within the frame a plurality of times and for outputting image data sets obtained by each photography operation; the photography control apparatus comprising:
input receiving means for receiving input of photography intervals between completion of a previous photography operation and initiation of a next photography operation;
photography control means for controlling the photography unit to perform a plurality of photography operations, based on the photography intervals received by the input receiving means; and
storage means for storing a plurality of template data sets, each of which includes photography intervals for each photography operation of the plurality of photography operations corresponding to a respective condition setting frame and are set in advance by each template data set; wherein:
the input receiving means reads out one of the template data sets from the storage means and receives input of the photography intervals for each condition setting frame, which is set in the template data set.

* * * * *